United States Patent [19]

Dlcastilho

[11] Patent Number: 5,033,464
[45] Date of Patent: Jul. 23, 1991

[54] COMBINATION ORAL SUCTION AND SCAVENGING APPARATUS

[76] Inventor: Raymond A. Dlcastilho, 48 Barbour Crescent, Ajax, Ontario, Canada, L1S 6Z6

[21] Appl. No.: 409,818

[22] Filed: Sep. 20, 1989

[51] Int. Cl.⁵ .............................................. A62B 7/00
[52] U.S. Cl. .............................. 128/205.19; 128/910
[58] Field of Search ............. 128/205.19, 910, 205.24, 128/204.18, 205.12, 203.12

[56] References Cited

U.S. PATENT DOCUMENTS

| | | | |
|---|---|---|---|
| 4,188,946 | 2/1980 | Watson et al. | 128/910 |
| 4,527,558 | 7/1985 | Hoenig | 128/205.19 |

FOREIGN PATENT DOCUMENTS

| | | | |
|---|---|---|---|
| 193174 | 9/1986 | European Pat. Off. | 128/910 |
| 2060404 | 5/1981 | United Kingdom | 128/910 |

Primary Examiner—Aaron J. Lewis
Attorney, Agent, or Firm—David W. Wong

[57] ABSTRACT

The compact combination oral suction and scavenging apparatus can be operated simultaneously or separately for oral suctioning and expired anaesthetic gases scavenging of a patient under sedation. It includes a main shut off valve for turning the entire apparatus on or off, and a separate shut off valve which can be operated selectively to disable the scavenger portion of the apparatus. A safety relief valve prevents sub-atmospheric or excessively high pressures from building up in the apparatus to affect the normal breathing pattern of a patient. The expiratory valve of the scavenging assembly is housed in a disposable chamber having a disposable transparent snap-on dome shaped cover such that the expiratory valve can be readily monitored visually, and the cover can be easily and quickly removed for manual manipulation or adjustment of the expiratory valve by the anaesthetist.

13 Claims, 4 Drawing Sheets

COMBINATION ORAL SUCTION AND SCAVENGING APPARATUS

BACKGROUND OF THE INVENTION

This invention relates to an apparatus suitable for oral suctioning and/or anaesthesia/analgesia gas scavenging particularly in a dental clinic.

Commonly in oral surgery, analgesic gas, such as nitrous oxide, better known as laughing gas, is used for inducing a state of sedation in a patient. This gas together with a volatile anaesthetic agent such as Ethrane, Forane, Halonthane or Penthrane is administered through a nose mask and it is inhaled by the patient until unconsciousness occurs. In order to maintain a toxic tree environment of the operating room, the expired gases exhaled by the patient must not be allowed to contaminate the air in the room. The vapours from the volatile agents are highly toxic and they can normally produce air pollution levels in an operating room in the range of 1500 to 2000 parts per million (PPM) in a matter of seconds. Such levels are considerably in excess of the maximum acceptable levels set in the standard by the Canadian Standards Association, which for waste anaesthetic gases in an operating environment are 25 to 30 PPM cf nitrous oxide and 0.25 to 0.50 PPM of any of the volatile agents.

A scavenging system coupled to the anaesthetic mask can be employed to remove the waste gases exhaled by the patient in order to maintain the cleanliness of the air in the operating room. Such system usually incorporates an expiratory or non-rebreathing valve located at the mask. During operation sometimes it may become necessary for the anaesthetist to have access to the expiratory valve quickly for manual adjustment of the valve due to the changing of breathing conditions of the patient under sedation. Current scavenging systems do not allow such access to the expiratory valve.

OBJECTS OF THE INVENTION

It is a principal object of the present invention to provide a compact apparatus which may be operated selectively as an oral suction device and/or a scavenging device for effectively removing the expired waste gases from a patient under sedation.

It is another object of the present invention to provide a combination oral suction and scavenging apparatus which can be installed in a clinical operating room easily and quickly.

It is another object of the present invention to provide a combination oral suction and scavenging apparatus having a unique expiratory valve adaptor which permits constant visual monitoring of the patient's breathing condition.

It is yet another object of the present invention to provide a combination oral suction and scavenging apparatus wherein the expiratory valve housing is simple in structure and can be readily opened for expeditious manual adjustment of the expiratory valve.

It is a further object of the present invention to provide a combination oral suction and scavenging apparatus wherein the expiratory valve housing is disposable to prevent any possible cross contamination in the use of the scavenging apparatus by different patients.

It is yet a further object of the present invention to provide a combination oral suction and scavenging apparatus having a unique safety valve to prevent sub-atmospheric or excessively high pressures from affecting the sedated patient's normal breathing pattern.

SUMMARY OF THE INVENTION

The combination oral suctioning and expired anaesthetic gases scavenging apparatus comprises a manifold block having a plurality of internal channels formed therein. An inlet socket means is mounted on the block and operative for coupling the internal channels to a vacuum source. The internal channels include a first channel in communication with the inlet port of the inlet socket means. A second channel extends transverse to the first channel and having an exit opening therein located at a first side of the manifold block. A suction fitting means mounted at the first side of the block and operative for attachment to a suction hose for oral suctioning. A third channel extends transverse to the first channel and second channel and downwardly to a bottom cavity of the manifold block. A fourth channel extends transverse to said third channel and outwardly from the bottom cavity to a second side of the manifold block. An exit fitting means mounted at the second side of the block and operative for mounting an auxiliary expiratory gases collection bag means thereto. A fifth channel extends transverse to the fourth channel and outwardly to a third opening located at the third side of the block. A hose fitting means is mounted at the third side of the block and operative for mounting a hose member thereto. An expiratory assembly means mounted to the hose member and having a mask means therein operative for receiving expired anaesthetic gases exhaled by a patient.

DETAILED DESCRIPTION OF THE PREFERRED EMBODIMENTS

Figure 3:
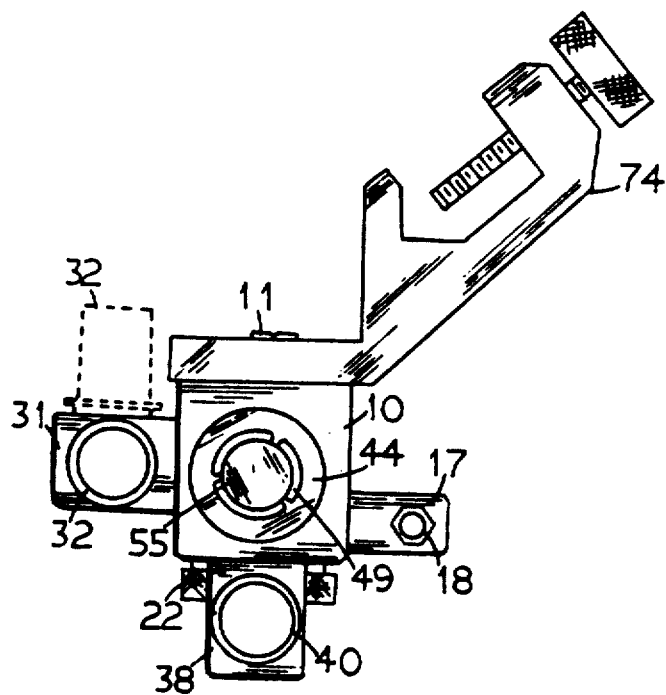
FIG. 3 is a bottom elevation view of the control block thereof.
Figure 4:
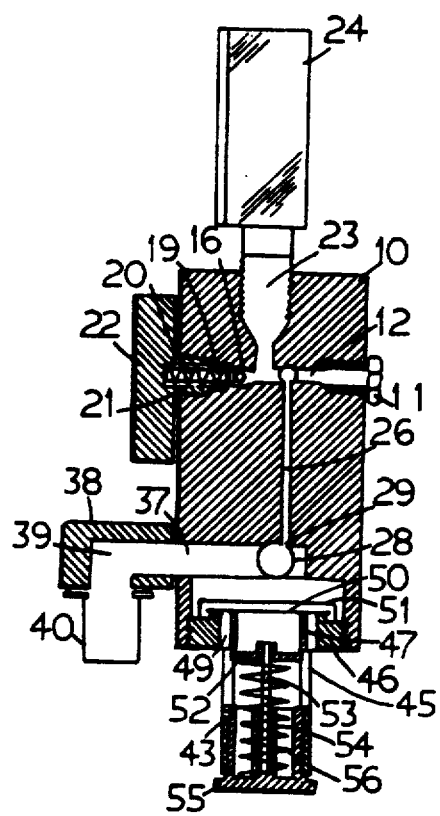
FIG. 4 is a section view of the control block thereof along section line IV—IV of FIG. 1.
Figure 5:
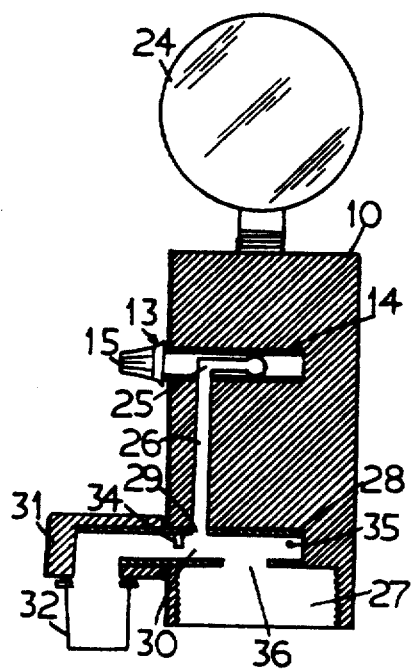
FIG. 5 is a section view oi the control block thereof along section line V—V oi FIG. 1.
Figure 7:
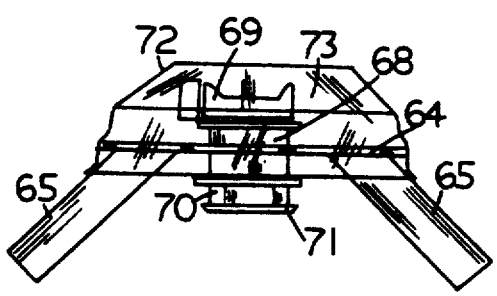
FIG. 7 is a side elevation view of the expiratory valve housing of the combination oral suction and scavenging apparatus according to the present invention.
Figure 8:
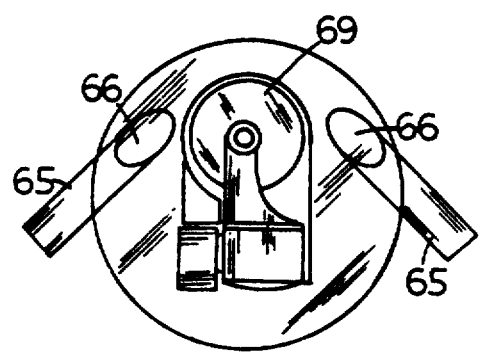
FIG. 8 is a top elevation view of the expiratory valve adaptor of the combination oral suction and scavenging apparatus according to the present invention with the covering dome removed.
Figure 9:
FIG. 9 is a side elevation view of the covering dome thereof.
Figure 10:
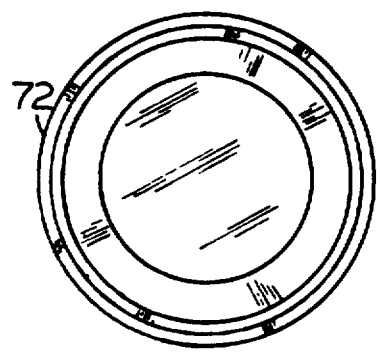
FIG. 10 is a top elevation view of the covering dome thereof.

With reference to the drawings wherein like reference numerals designate corresponding parts in the several views, the combination oral suction and scavenging apparatus according to the present invention has a substantially rectangular manifold block 10 having a threaded socket 11, as best shown in FIGS. 3 and 4, provided at a rear side therein for connection to a vacuum source such as a vacuum pump. A supply channel 12 formed in the manifold block 10 operatively in communication with the threaded socket 11 to conduct the vacuum into the block. The passage of the vacuum into the supply channel 12 is controlled by an inlet valve 13 in the form of a cylindrical tube 14 rotatably mounted to the block 10 and in perpendicular to the supply channel 12. The cylindrical tube 14 has two diametrically opposite openings formed on its side wall such that the cylindrical tube 14 may be turned to the position with one opening therein aligned with the threaded socket 11 and the other opening aligned with the supply channel 12 so as operatively to admit the vacuum into the supply channel 12. When the cylindrical tube 14 is turned with the openings on its side wall not aligned with the supply channel 12, the passage of the vacuum into the block 10 is shut off.

Figure 1:
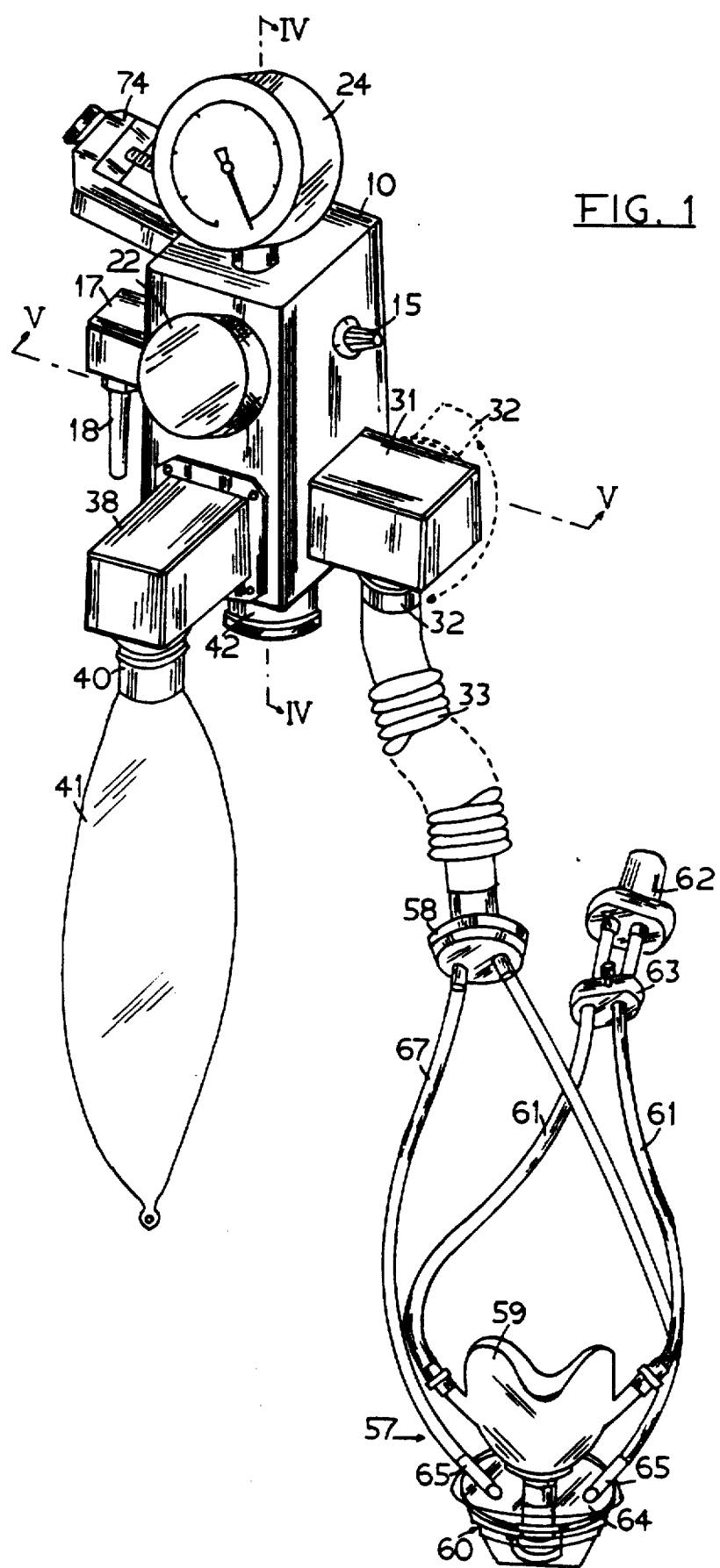
FIG. 1 is perspective front elevation view of the combination oral suction and scavenging apparatus according to the present invention.

A knob 15 is mounted to the end of the cylindrical tube 14, which extends outside of the manifold block 10. The channel 12 has a cross channel 16 extending sideways therefrom out to an attachment arm 17, and an suction fitting tube 18 is provided at the attachment arm 17 for slide attachment with a conventional oral suction hose operative for oral suction purposes. The amount of vacuum suction pressure at the suction fitting tube 18 is controlled by a regulator assembly 19, best shown in FIG. 4, provided at the other end of the channel 12 opposite to the socket 11. The regulator assembly 19 consists of primarily a springbiassed piston and shaft assembly 20 mounted in a threaded housing 21 rotatably mounted at the front end of the channel 11. The threaded housing 21 has a turning knob 22 at its front end such that the shaft 20 may be adjusted to cover over a selected portion of the port to the cross channel 16 in order to control the suctioning pressure of the oral suction hose. A vertical channel 23 extends from the supply channel 12 upwards to a port at the top of the manifold block 10 for mounting a vacuum gauge 24 which provides a means to monitor the vacuum pressure present in the manifold block 10. The cylindrical tube 14 also has a third side opening 25 which will become aligned with a downwardly extending vertical channel 26 whenever the diametrically opposite openings of the cylindrical tube 14 are aligned with the socket 11. The vertical channel 26 extends downwards to a bottom cavity 27 in the manifold block 10. A tubular member 28 is rotatably mounted to the manifold block 10 and is parallel to the cylindrical tube 14. The tubular member 28 has an opening 29 formed on its sidewall such that the tubular member 28 may be rotated to the position with the opening 29 aligned with the downwardly extending vertical channel 26 so that the cavity 30 of the tubular member 28 is in communication with the vertical channel 26. A rectangular hollow mounting block 31 is provided at the end of the rotatable tubular member 28 extending outside of the manifold block 10, and a scavenging fitting tube 32 is provided at the mounting block 31 for coupling to a corrugated hose 33 for connection to a scavenging mask. The tubular member 28 may be rotated by turning the mounting block 31, as best shown in FIGS. 1 and 3, through 90 degrees selectively so as to align or disalign the opening 29 in the tubular member 28 with the vertical channel 26. A transverse slot 34 is formed in the tubular member 28, which engages with a pin mounted at the manifold block 10 to guide the rotating movement of the tubular member 28. Also, a dimple 35 may be formed on the surface of the tubular member 28, which will engage with a detent means incorporated in the manifold block 10 to provide a click stop of the tubular member 28 when the opening 29 therein is in the position aligned with the downwardly extending vertical channel 26. In this position, a side opening 36 of the tubular member 28 is also in communication with the bottom cavity 27 of the manifold block 10.

The bottom cavity 27 is in communication with a side opening 37 formed in the manifold block 10. A hollow mounting block 38 is fixedly mounted to the side of the manifold block 10 such that the cavity 39 in the side mounting block 38 is in communication with the bottom cavity 27. An attachment fitting tube 40 is provided at the mounting block 38, and it is operative for receiving an auxiliary reservoir bag 41 to be mounted thereto. The auxiliary reservoir bag 41 is used as a precautionary means for storing temporarily any large volume of expired gases from the patient in the event that such large volume may be beyond the rate of gas evacuation of the system.

Figure 6:
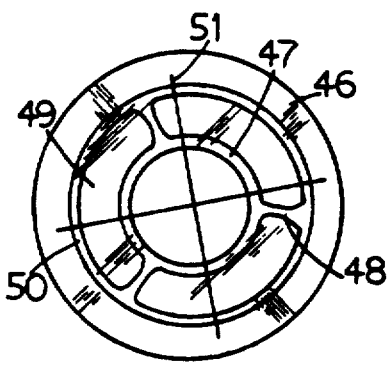
FIG. 6 is a top elevation view of the safety relief valve of the apparatus hereof.
Figure 11:
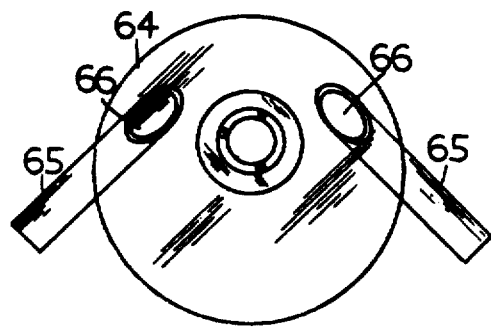
FIG. 11 is a top elevation view of the expiratory valve mounting plate thereof.

A safety relief valve 42 is located at the bottom cavity 27 of the manifold block 10. The safety relief valve 42 prevents sub-atmospheric or excessively high pressures from building up in the scavenging system to affect the patient's normal breathing pattern. The safety valve 42 consists of a cylindrical body 43 with threads formed in its inside surface. A wheel shaped upper body 44 is connected to the cylindrical body 43 by at least two integral posts 45. The upper body 44 has threads formed on it circumference for mounting the relief valve 42 threadingly to the bottom cavity 27 of the manifold block 10. The wheel shaped upper body 44 includes an outer ring 46 and a coaxially formed inner ring 47 spaced from the outer ring 46 and connected thereto by at least two and preferably three integral bars 48 such that arcuate openings 49 are provided between the inner ring 47 and the outer ring 46. A doughnut shaped thin diaphram 50, such as a mica disc is disposed over the top of the upper body 44 and it normally covers over the arcuate openings 49 by its gravity weight. The centre opening of the thin diaphram 50 is of the same size as the inner ring 47 and it is in register therewith. The thin diaphram 50 is prevented from displacing sideways by two inverted U-shaped wire guards 51 mounted to the top of the upper body 44 as best shown in FIG. 6. A circular disc 52 having a diameter slightly larger than the inner ring 47 is located below the latter. The circular disc 52 is supported by a pin 53 mounted at its centre and extends downwardly to engage a centre bore formed in a centre post 54 located in the cylindrical adjusting block 55. The cylindrical adjusting block 55 is threadingly mounted to the cylindrical body 43 of the safety valve 42. The circular disc 52 is maintained in abutment with the underside of the inner ring 47 by a bias spring 56. The biassing pressure of the spring 56 may be selectively adjusted by turning the adjusting block 55 to vary its vertical position relative to the cylindrical body 43.

The anaesthetic and scavenging mask assembly 57 is coupled to the corrugated hose 33 with a Y-coupler 58. The common rubber anaesthetic nose mask 59 is mounted to an expiratory control assembly 60. The anaesthetic nose mask 59 has two gas conducting tubes 61 connected to a T-coupler 62 for connection to a supply source of anaesthetic gases. An adjusting clamp 63 may be provided on the conducting tubes 61 as shown in FIG. 1.

The expiratory control assembly 60 comprises a circular baseplate 64 having two exit fittingtubes 65 extending downwards from two exit openings 66 formed therein. The exit fitting tubes 65 are for attachment to conducting hoses 67 which are, in turn, connected to the Y-coupler 58. A support cylinder is provided on the baseplate 64 and having therein an upper portion 68 extending upwards from the baseplate 64 and threads are formed at its top portion for mounting the expiratory valve 69. The lower portion 70 of the support cylinder extends downwards from the underside of the baseplate 64 and having a collar 71 formed therein. The lower portion 70 of the support cylinder is operative for mounting the anaesthetic nose mask 59 thereto. The collar 71 retains the nose mask 59 securely mounted to the cylinder. A transparent dome shape cover 72 is snap-fitted over the baseplate 64 and cooperated therewith to form an air-tight expiratory chamber 73 for enclosing the expiratory valve 69. Both the baseplate 64 and the dome shape cover 72 may be made of inexpensive disposable plastic material and the like.

Figure 2:
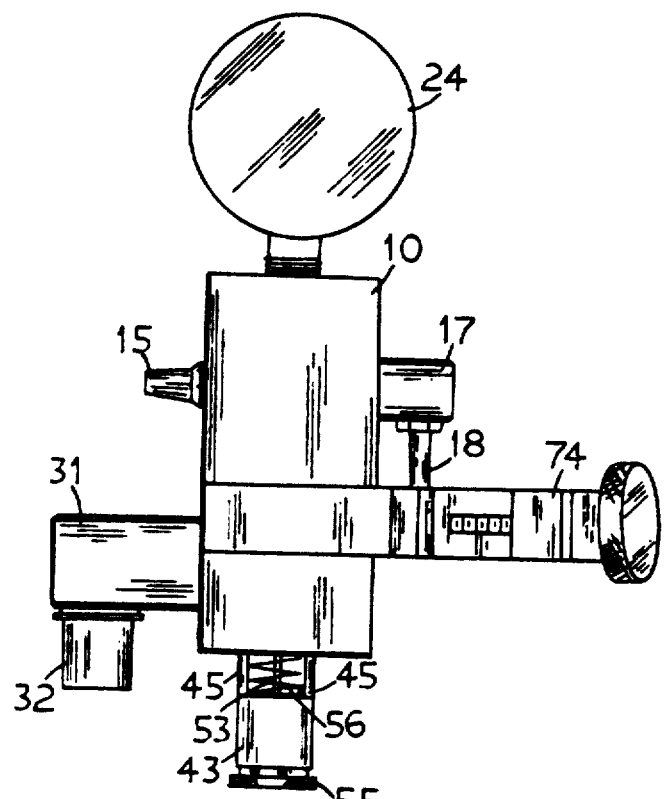
FIG. 2 is a rear elevation view of the control block thereof.

A clamping bracket 74, as best shown in FIGS. 1, 2 and 3, may be provided on the manifold block 10 for conveniently selectively mounting the manifold block to any post or vertical support of the equipment located adjacent to the operating chair or bed.

In operation, the compact manifold block 10 may be conveniently and quickly mounted to a vertical post or support of any equipment or fixture located adjacent to the operating chair or bed in the operating room. Vacuum pressure is supplied to the manifold block 10 by a hose connected to the socket 11 and to a vacuum source such as a vacuum pump or vacuum outlet normally provided in an operating room for various purposes. The inlet valve 13 may then be operated by turning the knob 15 to admit the vacuum pressure into the manifold block 10. In can be appreciated that the cylindrical tube 14 operated through the knob 15 serves as the main on and off control for the entire apparatus. An oral suction hose may then be attached to the suction fitting tube 18 in the conventional manner for oral suctioning purposes. The oral suctioning pressure can be effectively and selectively set by operating the turning knob 22 to adjust the regulator assembly 19. The vacuum pressure level present in the manifold block 10 is monitored by the vacuum gauge 24. The port to the cross channel 16 is opened in a selective amount by the shaft 20, when the regulator assembly 19 is operated, so as to allow a desired amount of suctioning pressure to be used for oral suctioning purposes.

For scavenging purposes, the expired gases from the patient is fed to the manifold block 10 from the expiratory valve assembly 60 through tubes 67 and corrugated hose 33 and scavenging fitting tube 32. The expired gases are then retrieved by the vacuum source for disposal. The rotatable mounting block 31 may be rotated through 90 degrees to displace the opening 29 in the tubular member 28 so that it is not in register with the vertical channel 26, thus turning off the scavenging portion oi the apparatus without affecting the operation oi the oral suctioning portion of the apparatus.

The safety relief valve 42 is designed to vent to the atmosphere when the pressure in the bottom cavity 27 of the manifold block 10 is less than −0.5 cm of water column, or in the event of excessively high back pressure of above 2.5 cm of water column. The mica disc 50 will be drawn upwards by the sub-atmospheric pressure of less than −0.5 cm of water column to vent the bottom cavity 27 through the arcuate openings 49, and until the desirable sub-atmospheric pressure is reached, the mica thin disc 50 will then fall back into its normal position to cover over the arcuate openings 49. Similarly, when the back pressure rises above 2.5 cm of water column, the excessive pressure will force the baffle circular disc 52 to displace away from the inner ring 47 thus venting the excessive pressure to the atmosphere until the pressure falls back to the desired level and the circular disc 52 will then return to its normal position by the biassing force exerted on it by the biassing spring 56 to abut against the inner ring 47.

In the event that an excessive amount of expired gases is present in the bottom cavity 27, of which it may be beyond the capacity of the apparatus to dispose, the excess gases will be collected by the auxiliary reservoir bag 41 for subsequent disposal.

In anaesthesia or analgesia, the nose mask 59 is pressed over the nose of the patient and the anaesthetic gases are supplied through the T-coupler 62 and rubber hoses 61 to the nose mask for inhalation by the patient. The expired gases exhaled by the patient is passed from the nose mask 59 through the support cylinder and the expiratory valve 69 into the expiratory chamber 73. The expired gases in the expiratory chamber 73 is subsequently drawn into the manifold block 10 through the conducting hoses 67 and the corrugated hose 33 for disposal.

Under sedation, the breathing of the patient causes a spring-biassed or gravity-biassed baffle in the expiratory valve 69 to open and close to release the expired gases into the expiratory chamber 73. The rhythm of the opening and closing of the baffle provides a visible means for judging the breathing pattern of the patient. In some instances, the anaesthetist may require to manually manipulate or adjust the baffle to affect the breathing pattern of the patient. Such visible means is impossible with the known expiratory valve assemblies heretofore in use. The transparent snap-on dome shaped cover 72 of the present invention enables the anaesthetist to visually monitor the movement of the baffle in the expiratory valve 69. Moreover, whenever it becomes necessary to manually manipulate the expiratory valve as indicated by patient response, the snap-on dome shape cover 72 can be quickly and easily removed with a push off action for the anaesthetist to have immediate access to the expiratory valve 69.

The dome shaped cover 72 and baseplate 64 may be made of an inexpensive transparent plastic material or the like such that the assembly can be disposed off after being used by each patient sc as to eliminate cross contamination among different patients. Furthermore, the plastic dome shape cover 72 can be manufactured easily and quickly by the well known heat mould injection process.

While the invention has been particularly shown and described with reference to a preferred embodiment thereof, it will be understood by those skilled in the art that various changes in form and detail may be made therein without departing from the spirit and scope of the invention.

I claim:

1. A combination oral suctioning and expired anaesthetic gases scavenging apparatus comprising, a manifold block member having a plurality of channels formed therein, an inlet socket means mounted on said block means and operative for coupling said channels to a vacuum source, said channels including a first channel in communication with said inlet socket means, a second channel extending transverse to said first channel and having an exit opening located at a first side of said block member, suction fitting means mounted at said first side of said block member and operative for attachment to a suction hose operative for oral suctioning, a third channel extending transverse to said first channel and said second channel, and downwardly to a bottom cavity in said manifold block member, a fourth channel extending transverse to said third channel and outwardly from said bottom cavity to a second opening located at a second side of said manifold block member, an exit fitting means mounted at said second side of said manifold block member and operative for mounting an auxiliary expiratory gases collection bag means thereto, a fifth channel extending transverse to said fourth channel and outwardly to a third opening located at a third side of said manifold block member, a hose fitting means mounted at said third side of said manifold block member and operative for connecting a hose member thereto, an expiratory assembly means mounted to said hose member and having a mask means therein operative for receiving expired anesthetic gases exhaled by a patient.

2. A combination oral suctioning and expired anaesthetic gases scavenging apparatus according to claim 1 including a cylindrical tube means rotatably mounted in said second channel and having one end therein extending outwards to a side of said manifold block member located opposite to said first side, two diametrically opposite openings formed in said cylindrical tube means, a knob member mounted at said one end of said cylindrical tube means and being operative to rotate said cylindrical tube means to selectively align said two diametrically opposite openings with said first channel for selectively admitting and shutting off vacuum pressure incoming to said manifold block member through said socket means.

3. A combination oral suctioning and expired anaesthetic gases scavenging apparatus according to claim 2 including a sixth channel extending transverse to said first channel and upwardly to a top opening of said manifold block member, a vacuum gauge means mounted at said top end of said sixth channel and operative to indicate the vacuum pressure in said manifold block member.

4. A combination oral suctioning and expired anaesthetic gases scavenging apparatus according to claim 3 wherein said first channel includes a first opening located at a front side of said manifold block member, a regulator assembly means mounted at said front opening, said regulator assembly means having a piston and shaft assembly mounted at a front end therein and operative by turning a rotary dial mounted at said regulator assembly means to cover selective portion of a port located at the side of said first channel and leading to said second channel whereby to meter a desirable amount of oral suctioning pressure to said suction hose mounted to said exit fitting means for oral suctioning purposes.

5. A combination oral suctioning and expired anaesthetic gases scavenging apparatus according to claim 4 wherein said cylindrical tube means includes a third opening formed therein, said third opening being in registry with said third channel when said two diametrically opposite openings are aligned with said first channel for conducting said vacuum pressure through said third channel to said bottom cavity of said manifold block member.

6. A combination oral suctioning and expired anaesthetic gases scavenging apparatus according to claim 5 including a safety relief valve means mounted at a bottom opening of said bottom cavity of said manifold block member, said safety relief valve means comprising, a substantially wheel shaped support body member having an outer ring member and an inner ring member disposed in a spaced manner coaxially from each other, at least two bar means connecting between said outer ring member and said inner ring member and forming at least two arcuate openings between said outer ring member and said inner ring member, a doughnut shaped thin disk member disposed over said support body member, said thin disk member normally covering over said arcuate openings and having an inner opening therein in registry over said inner ring member, a baffle member located below said inner ring member, said baffle member being normally spring-biassed to abut against said inner ring member.

7. A combination oral suctioning and expired anaesthetic gases scavenging apparatus according to claim 6 wherein said safety relief valve means includes a lower tubular body member located below and connected to said inner ring member by at least two post members, a threaded cylindrical member rotatably mounted within said tubular body member, a pin member secured underneath said baffle member and having a lower end therein supported by said threaded cylindrical member, a bias spring member located around said pin member and between said baffle member and said threaded cylindrical body member, said bias spring member normally exerting a biassing force on said baffle member to abut against said inner ring member, and said threaded cylindrical member being operative rotatably to displace vertically relative to said tubular body member to vary selectively said biassing force.

8. A combination oral suctioning and expired anaesthetic gases scavenging apparatus according to claim 7 wherein said expiratory assembly includes an expiratory valve means operative to monitor said expired anaesthetic gases being exhaled by the patient, said expiratory valve means being enclosed in a transparent housing comprising, a baseplate member having a top surface and a bottom surface, a tubular support member having an upper portion therein extending upwards from said top surface of said baseplate member, and a lower portion therein extending downwards from said bottom surface of said baseplate member, said upper portion of said tubular support member having a threaded upper end portion operative for mounting said expiratory valve means thereto, at least one exit opening formed in said baseplate member, hose fitting means located at said exit opening and extending downwardly from said bottom surface of said baseplate member, said hose fitting means being operative for coupling to said hose member, a transparent cover means removably snap-mounted over said baseplate member and in cooperation with said top surface of said baseplate member to form an air-tight enclosure for said expiratory valve means.

9. A combination oral suctioning and expired anaesthetic gases scavenging apparatus according to claim 8 wherein said baseplate member and said cover means are generally circular, and said cover having a general dome shape.

10. A combination oral suctioning and expired anaesthetic gases scavenging apparatus according to claim 9 wherein said baseplate member and said cover means are made of a plastic material and the like.

11. In a scavenging apparatus for expired anaesthetic gases wherein said gases are monitored by an expiratory valve means, an air-tight enclosure for housing said expiratory valve means comprising, a baseplate member having a top surface and a bottom surface, a tubular support member having an upper portion therein extending upwardly from said top surface of said baseplate member, and a lower portion therein extending downwardly from said bottom surface of said baseplate member, said upper portion having a threaded upper end portion operative for mounting said expiratory valve means thereto, and said lower portion having a collar formed adjacent a lower end portion therein, and said lower portion of said tubular support member being operative for mounting a nose mask thereto, at least one exit opening formed in said baseplate member, hose fitting means located at said exit opening and extending downwardly from said bottom surface of said baseplate member, said hose fitting means being operative for coupling to a scavenging device, a transparent cover means removably snap-mounted over said baseplate member and in cooperation with said top surface of said baseplate member forming said air-tight enclosure.

12. An air-tight enclosure for housing an expiratory valve means in a scavenging apparatus according to claim 11 wherein said baseplate member is a circular plate, and said cover means is a circular dome shape plastic cover.

13. An air-tight enclosure for housing an expiratory valve means in a scavenging apparatus according to claim 12 including two exit openings formed in said baseplate member and a hose fitting means extending from each one of said exit openings and downwardly from said bottom surface of said baseplate member, hose means coupled to said hose fitting means and operative for connection to an expired anaesthetic gases disposal means.

* * * * *

UNITED STATES PATENT AND TRADEMARK OFFICE
CERTIFICATE OF CORRECTION

PATENT NO. : 5,033,464
DATED : July 23, 1991
INVENTOR(S) : Delcatilho It is certified that error appears in the above-identified patent and that said Letters Patent is hereby corrected as shown below:

Title page, item [76]: Inventor's name should read
--Raymond A. Delcatilho--

Signed and Sealed this

First Day of October, 1991

Attest:

HARRY F. MANBECK, JR.

*Attesting Officer*      *Commissioner of Patents and Trademarks*